(12) United States Patent
Newman et al.

(10) Patent No.: US 12,651,656 B2
(45) Date of Patent: Jun. 9, 2026

(54) NEEDLE-GUIDANCE SYSTEMS, DEVICES, AND METHOD THEREOF INCLUDING RFID TECHNOLOGY

(71) Applicant: Bard Access Systems, Inc., Salt Lake City, UT (US)

(72) Inventors: Jon B. Newman, Centerville, UT (US); Sarah L. Creasy, Park City, UT (US); Kenneth W. Sykes, Bluffdale, UT (US); Jeanette E. Southard, Castleconnell (IE); Matthew J. Prince, Herriman, UT (US); Tab Robbins, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 804 days.

(21) Appl. No.: 17/008,085

(22) Filed: Aug. 31, 2020

(65) Prior Publication Data

US 2021/0065857 A1 Mar. 4, 2021

Related U.S. Application Data

(60) Provisional application No. 62/895,871, filed on Sep. 4, 2019.

(51) Int. Cl.
| | |
|---|---|
| *A61M 25/01* | (2006.01) |
| *G06F 21/62* | (2013.01) |

(Continued)

(52) U.S. Cl.
CPC ........ *G16H 10/65* (2018.01); *A61M 25/0105* (2013.01); *G06F 21/6245* (2013.01);

(Continued)

(58) Field of Classification Search
CPC . A61B 90/11; A61B 2034/2051; A61B 34/20; A61B 17/3403; A61B 90/98;

(Continued)

(56) References Cited

U.S. PATENT DOCUMENTS

| | | | |
|---|---|---|---|
| 6,370,411 | B1 | 4/2002 | Osadchy et al. |
| 6,611,793 | B1 | 8/2003 | Burnside et al. |

(Continued)

FOREIGN PATENT DOCUMENTS

| | | |
|---|---|---|
| WO | 12101551 A1 | 8/2012 |

OTHER PUBLICATIONS

PCT/US2020/048798 filed Aug. 31, 2020 International Search Report and Written Opinion dated Nov. 17, 2020.

*Primary Examiner* — Kevin C Sirmons
*Assistant Examiner* — William R Frehe
(74) *Attorney, Agent, or Firm* — Rutan & Tucker LLP

(57) ABSTRACT

A needle-guidance system is disclosed including single-patient equipment, multi-patient equipment, and an RFID reader-writer. The single-patient equipment can include a vascular access device ("VAD") having a needle and an RFID tag. The RFID tag can be incorporated into the VAD or packaging for the VAD. The console can be configured to automatically start needle tracking for a clinician on an integrated display screen of the console after receiving RFID-tag data from the RFID tag and processing with a processor of the console instructions of needle-tracking software provided by memory of the console for the needle tracking. The RFID reader-writer can be configured to read the RFID-tag data from the RFID tag and write additional RFID-tag data to the RFID tag. The RFID reader-writer can be provided with the packaging for the VAD or the multi-patient equipment. A method of the needle-guidance system is also disclosed.

13 Claims, 2 Drawing Sheets

SINGLE-PATIENT EQUIPMENT

MULTI-PATIENT EQUIPMENT

(51) Int. Cl.
    *G16H 10/65*       (2018.01)
    *G16H 20/17*       (2018.01)

(52) U.S. Cl.
    CPC ..... *G16H 20/17* (2018.01); *A61M 2025/0166*
        (2013.01); *A61M 2205/273* (2013.01); *A61M*
        *2205/583* (2013.01); *A61M 2205/60* (2013.01)

(58) Field of Classification Search
    CPC ........ A61M 2205/60; A61M 2205/273; A61M
                                   2025/0166
    See application file for complete search history.

(56)              References Cited

U.S. PATENT DOCUMENTS

| | | | |
|---|---|---|---|
| 6,792,390 | B1 | 9/2004 | Burnside et al. |
| 6,847,490 | B1 | 1/2005 | Nordstrom et al. |
| 6,861,954 | B2 | 3/2005 | Levin |
| 7,256,696 | B2 | 8/2007 | Levin |
| 7,299,981 | B2 | 11/2007 | Hickle et al. |
| 7,429,920 | B2 | 9/2008 | Smythe et al. |
| 7,443,296 | B2 | 10/2008 | Mezhinsky et al. |
| 7,518,502 | B2 | 4/2009 | Austin et al. |
| 7,559,483 | B2 | 7/2009 | Hickle et al. |
| 7,616,117 | B2 | 11/2009 | Streeb et al. |
| 7,787,958 | B2 | 8/2010 | Stevenson |
| 7,916,013 | B2 | 3/2011 | Stevenson |
| 7,934,648 | B2 | 5/2011 | Charles et al. |
| 7,983,763 | B2 | 7/2011 | Stevenson et al. |
| 8,033,174 | B2 | 10/2011 | Shin et al. |
| 8,044,778 | B2 | 10/2011 | Monroe |
| 8,114,063 | B2 | 2/2012 | Sacco et al. |
| 8,206,374 | B2 | 6/2012 | Duane et al. |
| 8,226,610 | B2 | 7/2012 | Edwards et al. |
| 8,233,963 | B2 | 7/2012 | Hartmann et al. |
| 8,385,972 | B2 | 2/2013 | Bochenko et al. |
| 8,600,478 | B2 | 12/2013 | Verard et al. |
| 9,101,298 | B2 | 8/2015 | Hossack et al. |
| 9,138,516 | B2 | 9/2015 | Vischer et al. |
| 9,208,362 | B1 | 12/2015 | Fink et al. |
| 9,218,452 | B2 | 12/2015 | Varna et al. |
| 9,223,934 | B2 | 12/2015 | Hussain et al. |
| 9,237,919 | B2 | 1/2016 | Maschke |
| 9,278,177 | B2 | 3/2016 | Edwards et al. |
| 9,283,334 | B2 | 3/2016 | Mantell et al. |
| 9,550,021 | B2 | 1/2017 | Beden et al. |
| 9,622,808 | B2 | 4/2017 | Beller et al. |
| 2004/0008123 | A1 | 1/2004 | Carrender et al. |
| 2004/0230116 | A1 | 11/2004 | Cowan et al. |
| 2004/0231772 | A1 | 11/2004 | Leonard et al. |
| 2006/0073048 | A1* | 4/2006 | Malackowski ...... A61M 3/0208 |
| | | | 417/474 |
| 2008/0061153 | A1 | 3/2008 | Hickle et al. |
| 2008/0147529 | A1* | 6/2008 | Kreiner ............... G06Q 10/087 |
| | | | 340/572.1 |
| 2008/0221549 | A1 | 9/2008 | Cohen |
| 2008/0319510 | A1 | 12/2008 | Simpson et al. |
| 2009/0065565 | A1 | 3/2009 | Cao |
| 2009/0118612 | A1 | 5/2009 | Grunwald et al. |
| 2009/0156926 | A1 | 6/2009 | Messerly et al. |
| 2009/0264866 | A1 | 10/2009 | Powell |
| 2010/0161345 | A1 | 6/2010 | Cain et al. |
| 2011/0208117 | A1 | 8/2011 | Hawkins |
| 2012/0185267 | A1 | 7/2012 | Kamen et al. |
| 2012/0220879 | A1 | 8/2012 | Fandrey et al. |
| 2014/0024931 | A1 | 1/2014 | Winston et al. |
| 2014/0031674 | A1* | 1/2014 | Newman ............. A61B 8/0841 |
| | | | 600/424 |
| 2014/0180110 | A1 | 6/2014 | Schmedling |
| 2014/0184391 | A1* | 7/2014 | Elizondo, II ....... G06K 7/10356 |
| | | | 340/10.1 |
| 2014/0276587 | A1* | 9/2014 | Imran ................... A61M 5/148 |
| | | | 604/506 |
| 2014/0276603 | A1 | 9/2014 | Magee et al. |
| 2014/0323869 | A1 | 10/2014 | Jin et al. |
| 2015/0012072 | A1 | 1/2015 | Johnson et al. |
| 2015/0196369 | A1 | 7/2015 | Glossop |
| 2015/0343173 | A1* | 12/2015 | Tobescu ........... A61M 25/0017 |
| | | | 604/246 |
| 2016/0199028 | A1 | 7/2016 | Jeon et al. |
| 2016/0220325 | A1 | 8/2016 | Jeon et al. |
| 2016/0239696 | A1 | 8/2016 | Mats et al. |
| 2016/0278739 | A1 | 9/2016 | Pelissier et al. |
| 2016/0283759 | A1 | 9/2016 | Forster |
| 2017/0007200 | A1 | 1/2017 | Hagy et al. |
| 2017/0079681 | A1* | 3/2017 | Burnside ............. A61B 90/98 |
| 2017/0103498 | A1 | 4/2017 | Waters et al. |
| 2018/0000337 | A1* | 1/2018 | Chen ..................... A61B 18/22 |
| 2018/0310955 | A1* | 11/2018 | Lindekugel .......... A61B 8/0891 |
| 2020/0061340 | A1* | 2/2020 | Mixter ................ A61B 8/4466 |

\* cited by examiner

NEEDLE-GUIDANCE SYSTEMS, DEVICES, AND METHOD THEREOF INCLUDING RFID TECHNOLOGY

PRIORITY

This application claims the benefit of priority to U.S. Provisional Application No. 62/895,871, filed Sep. 4, 2019, which is incorporated by reference in its entirety into this application.

BACKGROUND

Radiofrequency identification ("RFID") technology is an automatic identification and data capture ("AIDC") technology used across many different industries to automatically identify objects, capture data about the objects, and load the data into electronic devices or systems for processing the data—all with little to no human action. While RFID technology is already used in the medical industry to track and manage inventory, assets, and patients, improvements are needed in at least operating room management to streamline use of medical devices and provide better patient outcomes.

Disclosed herein are needle-guidance systems, devices, and methods thereof including RFID technology that addresses at least the foregoing.

SUMMARY

Disclosed herein is a needle-guidance system including, in some embodiments, single-patient equipment, multi-patient equipment, and an RFID reader-writer provided with the single-patient equipment or the multi-patient equipment. The single-patient equipment includes a vascular access device ("VAD") having a needle and an RFID tag. The needle includes a magnet or a magnetizable region about a distal-end portion of the needle configured for magnetically tracking the needle near or in a patient. The RFID tag is incorporated into the VAD or packaging for the VAD. The multi-patient equipment includes a console optionally having a number of ports including an RFID-reader port. The console is configured to automatically start needle tracking for a clinician on an integrated display screen of the console after receiving RFID-tag data from the RFID tag, validating the VAD, and processing with a processor of the console instructions of needle-tracking software provided by memory of the console for the needle tracking. The RFID reader-writer is configured to read the RFID-tag data from the RFID tag and write additional RFID-tag data to the RFID tag. The RFID reader-writer is provided with the packaging for the VAD or the multi-patient equipment.

In some embodiments, the RFID-tag data is encrypted.

In some embodiments, the RFID-tag data includes needle characteristics of the needle. The needle characteristics are selected from needle length, needle gauge, needle bevel, magnetic strength of the magnet, geometric length of the magnet, magnetic length of the magnet, magnetic-alignment parameters of the magnetic relating offsets of a magnetic-field axis to a physical axis.

In some embodiments, the console is configured to correctly identify the needle from the needle characteristics, accurately guide insertion of the needle into the patient, and display for the clinician a location of the needle in the patient on the display screen.

In some embodiments, the console includes a catheter-determination algorithm configured to select a catheter of an appropriate gauge for use with the VAD in accordance with the needle characteristics.

In some embodiments, the console includes a use-enforcement algorithm configured to enforce a predefined maximum number of uses of the VAD.

In some embodiments, the predefined maximum number of uses of the VAD is a single use of the VAD.

In some embodiments, the console is configured to automatically stop needle tracking upon exceeding the predefined number of uses of the VAD.

In some embodiments, the console includes a patient database configured for associating the VAD with an active patient profile for the patient by way of the RFID-tag data.

In some embodiments, the additional RFID-tag data includes a timestamp for each date and time the RFID-tag data is read from the RFID tag including a starting timestamp and a stopping timestamp.

In some embodiments, the console is configured to simultaneously store in a device database of the console identifying information for the VAD from the RFID-tag data as well as the starting and stopping timestamps for calculating dwell time for the needle of the VAD.

In some embodiments, the console includes a reporting algorithm configured to report on the display screen a rate of unique VADs used with the console over one or more periods of time from the device database.

In some embodiments, the RFID reader-writer is provided in a magnetizer tray of the packaging for the VAD. The magnetizer tray includes an RFID-reader port configured to be connected to the RFID-reader port of the console by a cable.

In some embodiments, the magnetizer tray is configured to magnetize the magnetizable region of the needle while reading the RFID-tag data from the RFID tag.

In some embodiments, the RFID reader-writer is a handheld RFID reader-writer provided with the multi-patient equipment. The handheld RFID reader-writer includes an RFID-reader port configured to be connected to the RFID-reader port of the console by a cable.

In some embodiments, the RFID reader-writer is an internal RFID reader-writer of the console provided with the multi-patient equipment.

Also disclosed herein is a method of a needle-guidance system including, in some embodiments, a step of obtaining a VAD for use with a patient. The VAD has a needle including a magnet or a magnetizable region about a distal-end portion of the needle. The VAD also has an RFID tag incorporated into the VAD or packaging for the VAD. The method also includes a step of accessing by a clinician a console having a number of ports including an RFID-reader port. The method also includes a step of processing with a processor of the console instructions of needle-tracking software provided by memory of the console for needle tracking. The method also includes a step of reading RFID-tag data from the RFID tag with an RFID reader-writer and, optionally, a step of writing additional RFID-tag data to the RFID tag. The method also includes a step of validating the VAD by way of the RFID-tag data. The method also includes a step of needle tracking on an integrated display screen of the console after receiving the RFID-tag data from the RFID tag.

In some embodiments, the step of reading the RFID-tag data from the RFID tag with the RFID reader-writer includes reading encrypted RFID-tag data from the RFID tag.

In some embodiments, the step of reading the RFID-tag data from the RFID tag with the RFID reader-writer includes reading needle characteristics of the needle. The needle characteristics are selected from needle length, needle gauge, needle bevel, magnetic strength of the magnet, geometric length of the magnet, magnetic length of the magnet, and magnetic-alignment parameters of the magnetic relating offsets of a magnetic-field axis to a physical axis.

In some embodiments, the method further includes a step of correctly identifying with the console the needle from the needle characteristics. The method also includes a step of accurately guiding insertion of the needle into the patient on the display screen. The method also includes a step of displaying for the clinician on the display screen a location of the needle in the patient.

In some embodiments, the method further includes a step of selecting with a catheter-determination algorithm of the console a catheter of an appropriate gauge for use with the VAD in accordance with the needle characteristics.

In some embodiments, the method further includes a step of enforcing with a use-enforcement algorithm of the console a predefined maximum number of uses of the VAD.

In some embodiments, the step of enforcing the predefined maximum number of uses of the VAD includes enforcing a single use of the VAD.

In some embodiments, the method further includes a step of automatically stopping the needle tracking with the console upon exceeding the predefined number of uses of the VAD.

In some embodiments, the method further includes a step of associating the VAD with an active patient profile for the patient in a patient database of the console by way of the RFID-tag data.

In some embodiments, the step of writing the additional RFID-tag data to the RFID tag includes writing a timestamp for each date and time the RFID-tag data is read from the RFID tag including a starting timestamp and a stopping timestamp.

In some embodiments, the method further includes a step of simultaneously storing in a device database of the console identifying information for the VAD from the RFID-tag data as well as the starting and stopping timestamps. The method also includes a step of calculating dwell time for the needle of the VAD in accordance with the starting and stopping timestamps.

In some embodiments, the method further includes a step of reporting on the display screen a rate of unique VADs from the device database used with the console over one or more periods of time. The console includes a reporting algorithm configured for the reporting.

In some embodiments, the method further includes a step of connecting an RFID-reader port of the RFID reader-writer to the RFID-reader port of the console by a cable. The step of obtaining the VAD includes obtaining the RFID reader-writer as part of a magnetizer tray of the packaging for the VAD.

In some embodiments, the method further includes a step of magnetizing the magnetizable region of the needle with the magnetizer tray during the step of reading the RFID-tag data from the RFID tag.

In some embodiments, the method further includes a step of connecting an RFID-reader port of a handheld RFID reader-writer to the RFID-reader port of the console by a cable. The method also includes a step of reading the RFID-tag data from the RFID tag with the handheld RFID reader-writer each time a procedural event of a number of procedural events is performed. Each procedural event is selected from inserting the needle of the VAD into the patient, drawing blood from the patient, selecting a medication for infusion, infusing the medication into the patient, observing morbidity, pulling the VAD from the patient, and exchanging the VAD. The method also includes a step of logging by the console the procedural events in a procedural event database.

These and other features of the concepts provided herein will become more apparent to those of skill in the art in view of the accompanying drawings and following description, which describe particular embodiments of such concepts in greater detail.

DRAWINGS

DESCRIPTION

Figure 1:
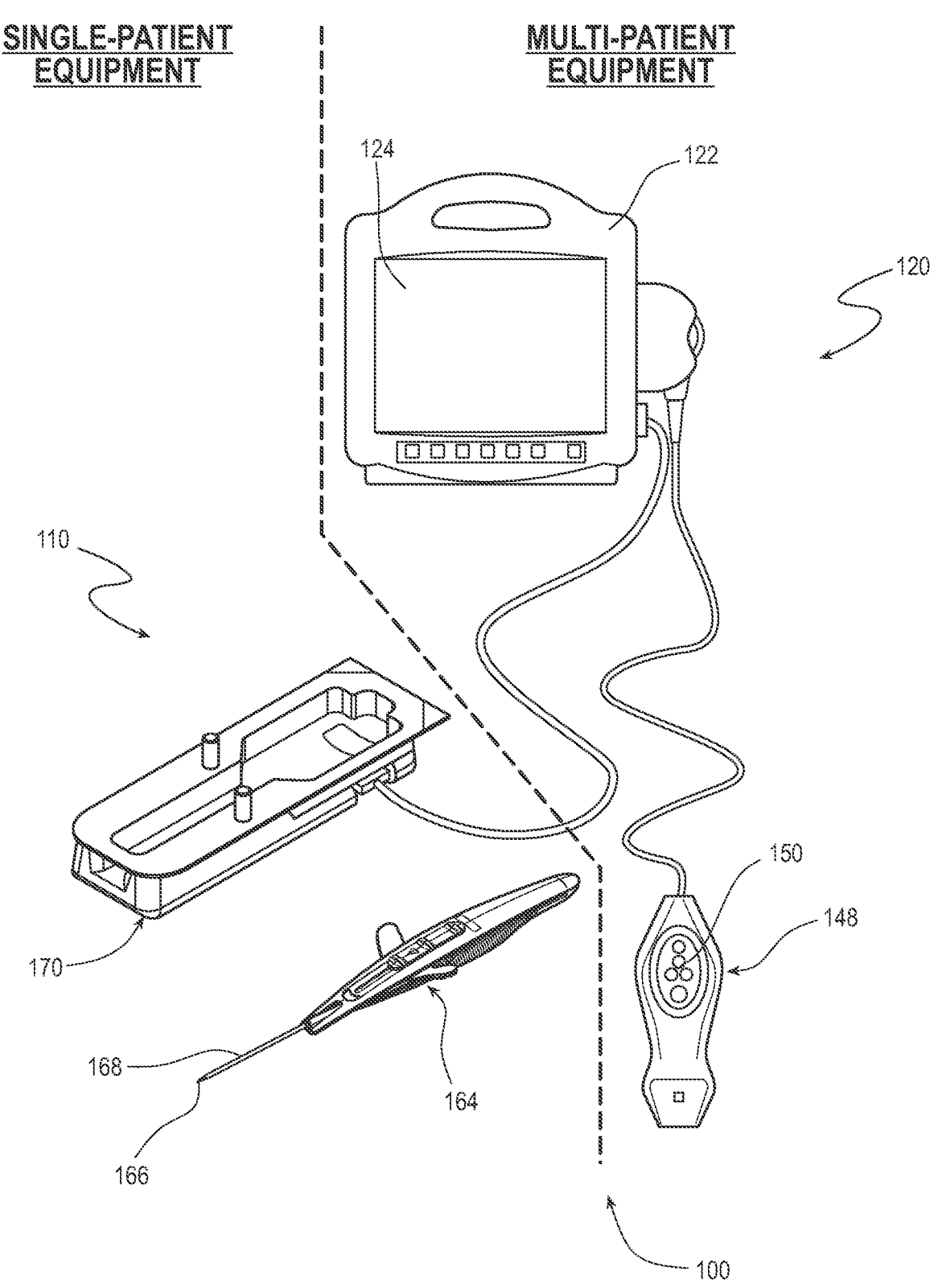
FIG. 1 illustrates a needle-guidance system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, improvements are needed in at least operating room management to streamline use of medical devices and provide better patient outcomes. Disclosed herein are needle-guidance systems, devices, and methods thereof including RFID technology that addresses at least the foregoing.

Needle-Guidance Systems and Devices

Figure 2:
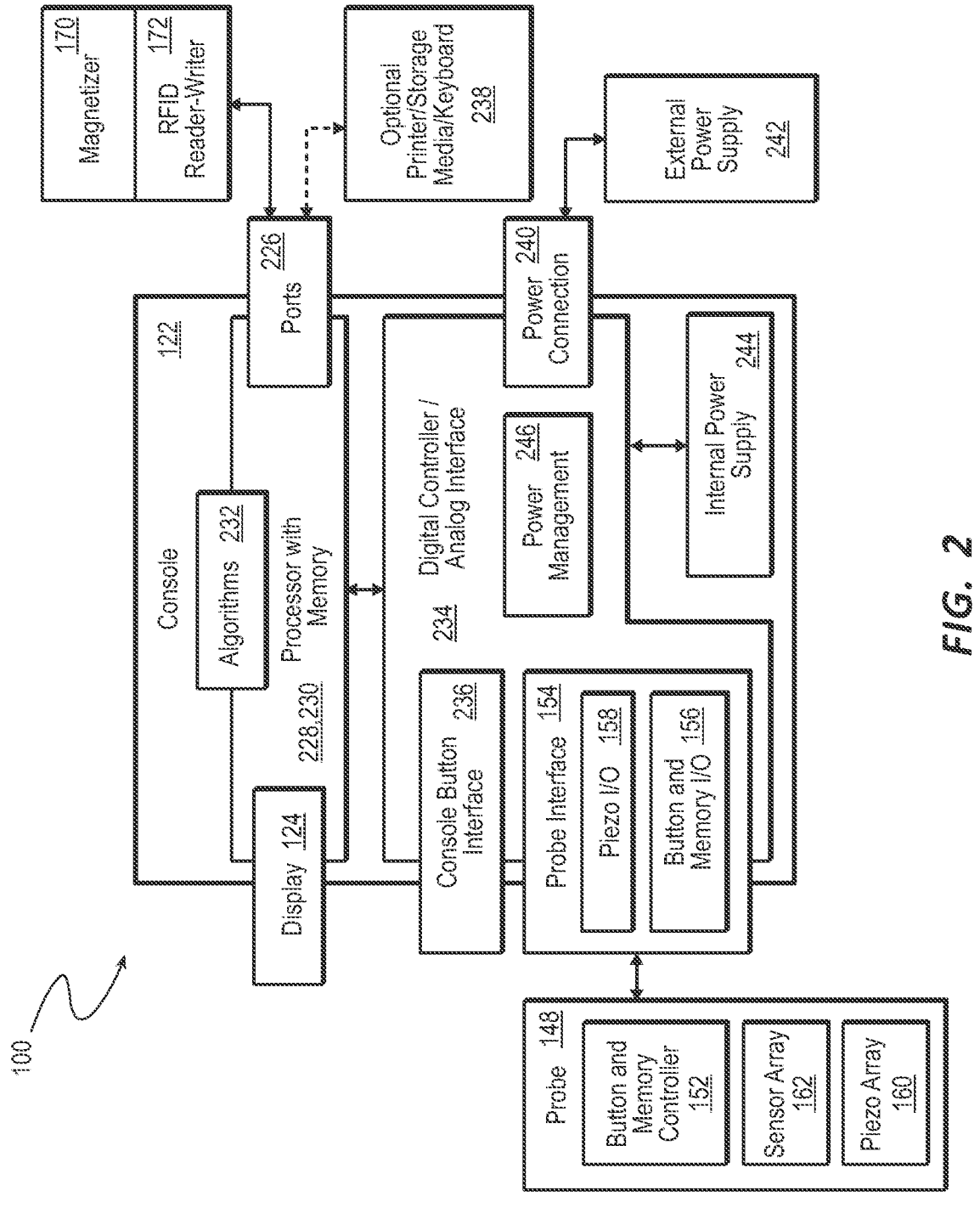
FIG. 2 illustrates a block diagram of the needle-guidance system in accordance with some embodiments.

FIG. 1 illustrates a needle-guidance system 100 in accordance with some embodiments. FIG. 2 illustrates a block diagram of the needle-guidance system 100 in accordance with some embodiments.

As shown, the needle-guidance system 100 includes single-patient equipment 110 and multi-patient equipment 120. While an RFID reader or RFID reader-writer is provided with either the single-patient equipment 110 or the multi-patient equipment 120 in accordance with different embodiments of the needle-guidance system 100, the needle-guidance system 100 of FIG. 1 includes the RFID reader or RFID reader-writer in a magnetizer tray as set forth in more detail below. However, it should be understood the RFID reader or RFID reader-writer in the magnetizer tray is but one embodiment of the RFID reader or RFID reader-writer in the needle-guidance system 100. Indeed, the console 122 set forth below, itself, can include an internal RFID reader or RFID reader-writer.

Beginning with the multi-patient equipment 120, the multi-patient equipment 120 includes a console 122 having an integrated display screen 124 and a number of ports 226 including an RFID-reader port configured to connect the RFID reader or RFID reader-writer. However, if the console 122 includes an internal RFID reader or RFID reader-writer, the console 122 need not include the RFID-reader port.

The console 122 houses a number of components of the needle-guidance system 100. The number of components includes a processor 228 and memory 230 for controlling needle-guidance-system function and executing various algorithms 232 during operation of the needle-guidance system 100. For example, the processor 228 is configured to process instructions of needle-tracking software provided by the memory 230 for needle tracking. The number of components also includes a digital controller and analog interface 234, which governs interfacing between various system components such as the processor 228, the memory 230, and additional components of the needle-guidance system 100 such as a button interface 236 of the console 122.

The display screen 124 is configured to display graphical and textual information to a clinician during a percutaneous procedure. For example, the display screen 124 can be a liquid crystal display ("LCD"). A standalone monitor having a display screen is an alternative to the display screen 124 being integrated into the console 122.

Again, the console 122 includes the number of ports 226, which can include the RFID-reader port configured to connect the RFID reader or RFID reader-writer. The number of ports 226 also include other ports such as one or more universal-serial-bus ("USB") ports for connecting optional components 238 including a printer, one or more storage devices, a keyboard, a mouse, or the like.

A power connection 240 of the console 122 is configured to provide an operable connection to an external power supply 242. An internal power supply 244 (e.g., a battery) can also be employed, either together with or exclusive of the external power supply 242. Power management circuitry 246 is included with the digital controller and analog interface 234 of the console 122 to regulate power use and distribution.

The multi-patient equipment 120 further includes an ultrasound probe 148 for imaging an internal portion of a body of a patient prior to a percutaneous procedure such as insertion of a needle, placement of a catheter, or the like to access the portion of the body of the patient. For example, the ultrasound probe 148 can be employed in connection with imaging a vessel such as a vein in preparation for insertion of a needle or placement of a catheter into the vessel. Such imaging provides real-time ultrasound guidance and reduces complications typically associated with the foregoing such as inadvertent arterial punctures, hematomas, or the like.

The ultrasound probe 148 includes a number of control buttons 150 for controlling the ultrasound probe 148 and certain aspects of the needle-guidance system 100, thus eliminating a need for a clinician to reach out of a sterile field established about a patient to control the ultrasound probe 148 or the needle-guidance system 100. For example, the control buttons 150 can be used to immediately call up a desired mode of the needle-guidance system 100 to the display screen 124 by a clinician to assist in a percutaneous procedure.

The ultrasound probe 148 includes a button and memory controller 152 for governing operation of the control buttons 150 and the ultrasound probe 148. The button and memory controller 152 can include non-volatile memory such as electrically erasable programmable read-only memory ("EEPROM"). The button and memory controller 152 is in electrical communication with a probe interface 154 of the console 122, which includes a button and memory input/output component 156 for interfacing with the button and memory controller 152, as well as a piezo input/output component 158 for interfacing with a piezoelectric array 160 of the ultrasound probe 148.

The ultrasound probe 148 houses the piezoelectric array 160 in a head of the ultrasound probe 148. The piezoelectric array 160 is configured to emit ultrasonic pulses and receive echoes thereof reflected off internal anatomy of a patient when the head of the ultrasound probe 148 is placed against skin of the patient proximate a prospective insertion site.

The ultrasound probe 148 includes a sensor array 162 having a number of magnetic sensors (e.g., 5 magnetic sensors) embedded within a housing of the ultrasound probe 148 configured to track a magnetized needle such as that of the VAD 164 set forth below by way of a magnetic field associated with the needle. The magnetic sensors of the sensor array 162 are configured to detect the magnetic field of the needle in three dimensions, which enables the pitch and yaw of the needle to be determined as well. Thus, the sensor array 162 enables location and orientation of a magnetized needle to be tracked by way of a magnetic field associated with the needle.

The magnetic sensors of the sensor array 162 can be disposed in an annular configuration about or near the head of the ultrasound probe 148. That said, the magnetic sensors can be arranged in other configurations such as in semi-circular or rectangular configuration. Each magnetic sensor of the sensor array 162 includes three orthogonal sensor coils configured as Hall-effect sensors. Such magnetic sensors can be purchased from, for example, Honeywell Sensing and Control of Morristown, N.J. However, other types of magnetic sensors could be employed. As an alternative to the foregoing magnetic sensors, the sensor array 162 can include a number of one-dimensional magnetic sensors arranged to achieve 1-, 2-, or 3-dimensional detection capability.

The multi-patient equipment can further include a hand-held RFID reader or RFID reader-writer (not shown) as an alternative to the RFID reader or RFID reader-writer 172 set forth below or in addition to the RFID reader or RFID reader-writer 172 set forth below. The handheld RFID reader or RFID reader-writer includes an RFID-reader port config-ured to be connected to the RFID-reader port of the console 122 by a cable.

The handheld RFID reader or RFID reader-writer is configured to read RFID-tag data from the RFID tag for the VAD 164 or the like as set forth below, which enables the console 122 to customize its operation in accordance with needle characteristics of a needle such as the needle 166 of the VAD 164. In addition, the handheld RFID reader-writer is configured to write additional RFID-tag data to the RFID tag. The additional RFID-tag data can include a timestamp for each date and time the RFID-tag data is read from the RFID tag including a starting timestamp and a stopping timestamp. The console 122 can be configured to simulta-neously store in a device database of the console 122 identifying information for a VAD from the RFID-tag data as well as the starting and stopping timestamps for calcu-lating dwell time for a needle such as the needle 166 of the VAD 164.

The console 122 can include an internal RFID reader or RFID reader-writer as an alternative to the RFID reader or RFID reader-writer 172 or the handheld RFID reader or RFID reader-writer or in addition thereto. Indeed, the RFID reader or RFID reader-writer can be inside a body of the console 122 with a marked or unmarked region on an outside of the console 122 to which the RFID tag of the VAD 164 or the like needs to be brought into proximity for reading or writing. The internal RFID reader or RFID reader-writer enables the console 122 to customize its operation in accor-dance with needle characteristics of a needle such as the needle 166 of the VAD 164. In addition, the internal RFID reader-writer is configured to write additional RFID-tag data to the RFID tag. The additional RFID-tag data can include a timestamp for each date and time the RFID-tag data is read from the RFID tag including a starting timestamp and a stopping timestamp. The console 122 can be configured to simultaneously store in the device database of the console 122 identifying information for a VAD from the RFID-tag data as well as the starting and stopping timestamps for calculating dwell time for a needle such as the needle 166 of the VAD 164.

With respect to customized operation of the console 122 in accordance with needle characteristics of a needle, the console 122 can be configured to automatically start needle tracking for a clinician on the display screen 124 of the console 122 after receiving the RFID-tag data from the RFID tag and correctly identifying the needle from the needle characteristics, whereby the console 122 accurately guides insertion of the needle into a patient and displays for a clinician a location of the needle in the patient on the display screen 124. Correctly identifying the needle from the needle characteristics can include validating compatibility of a VAD with one or more additional medical devices, a particular percutaneous procedure, or the like such as by checking look-up tables in the memory 230 or online databases. Such customized operation of the console 122 makes percutaneous procedures more efficient.

The console 122 can include a use-enforcement algorithm of the algorithms 232 configured to enforce a predefined maximum number of uses of a VAD such as the VAD 164. The predefined maximum number of uses is determined, at least in part, by a number of times the RFID reader-writer reads the RFID-tag data from the VAD. The predefined maximum number of uses of a VAD can be a single use of the VAD or more than a single use of the VAD. Whether the predefined maximum number of uses of the VAD is a single use or more than a single use of the VAD, the console 122 can be configured to automatically stop the needle tracking upon exceeding the predefined number of uses of the VAD. The console 122 can be configured to automatically start the needle tracking again upon receiving other RFID-tag data from another RFID incorporated into another VAD or master RFID-tag data from a master RFID tag. The master RFID tag is configured to enable training nurses and sales represen-tatives to bypass the predefined number of uses of a dem-onstration VAD, which can be an authentic VAD optionally restricted to demonstration use only.

The console 122 can include a reporting algorithm of the algorithms 232 configured to report on the display screen 124 a rate of unique VADs used with the console 122 over one or more periods of time (e.g., hours, days, weeks, months, etc.) such as 20 VADs/day, 300 VADs/month, or the like from the device database.

The console 122 can include a patient database configured for associating a VAD with an active patient profile for a patient by way of the RFID-tag data. Should one or more additional VADs be used during a same percutaneous pro-cedure, the patient database can be configured for further associating the one or more additional VADs with the active patient profile. For each VAD in the active patient profile, a needle stick with the VAD is assumed. Upon changing to a new patient and, thus, a new active patient profile, the patient database is cleared for associating a new VAD with the new active patient profile.

The console 122 can also be configured to automatically identify a clinician if the clinician has a unique RFID tag associated with him or her (e.g., an RFID tag incorporated into a badge) that the RFID reader or RFID reader-writer can read. The unique RFID tag can be used to log in to the console 122 or minimize steps used to log in to the console 122, load user preferences for the clinician in the needle-tracking software of the console 122, document the clini-cian's frequency of use of the console 122 or like consoles, document the clinician's number and type of VADs placed, identify the number real-time hours or training hours for the console 122 or like consoles, as well as document a number of uses of the console 122 or like consoles with or without using the needle-tracking software.

Turning to the single-patient equipment 110, the single-patient equipment includes a VAD 164 having a needle 166 and an RFID tag (not shown). The VAD 164 further includes a catheter 168, within which the needle 166 is disposed. It should be understood that the VAD 164 is but one example of a medical device including a magnetized or magnetizable needle that can be tracked with the console 122 and the ultrasound probe 148 of the needle-guidance system 100. Other VADs need not include a catheter. As such, description of the needle-guidance system 100 should not be considered limited with respect to the VAD 164 unless mandated by a particular feature of the VAD 164.

The needle 166 includes a magnet or a magnetizable region about a distal-end portion of the needle 166 configured for magnetically tracking the needle 166 near or in a patient with the console 122 and the ultrasound probe 148 of the needle-guidance system 100. Magnetically tracking the needle 166 near the patient is useful for tracking the location and the orientation of the needle 166 prior to inserting the needle 166. In the context of VAD 164, the needle is disposed in the catheter 168 of the VAD 164 such that the needle 166 provides initial access to a vessel of patient for subsequent access by the catheter 168.

The needle 166 can be stainless steel such as Society of Automotive Engineers ("SAE") Grade 304 stainless steel, which includes a relatively high nickel content between about 8 and 10.5% (w/w), a relatively high amount of chromium between about 18 to 20% (w/w), other major alloying elements including manganese, silicon, and carbon, and a remainder of iron; however, other suitable needle materials capable of being magnetized can be used. So configured, the needle 166 produces a magnetic field that is detectable by the sensor array 162 of the ultrasound probe 148 so as to enable the location and orientation of the needle 166 to be tracked by the needle-guidance system 100.

The RFID tag for the VAD 164 is incorporated into either the VAD 164 itself or packaging for the VAD 164. For example, the RFID tag can be incorporated into a hub of the VAD 164, provided on a card as part of the packaging for the VAD 164, incorporated in a portion of a tray (e.g., a top tray of the magnetizer tray 170) as part of the packaging of the VAD 164, or the like. The RFID tag for the VAD 164 includes RFID-tag data for the VAD 164, which data can be encrypted making counterfeiting difficult. The RFID-tag data can include needle characteristics of the needle 166 selected from at least needle length, needle gauge, needle bevel, magnetic strength of the magnet, geometric length of the magnet used in tracking, magnetic length or pole-to-pole length of the magnet, magnetic-alignment parameters of the magnetic relating offsets of a magnetic-field axis to a physical axis. Such needle characteristics are useful to the needle-tracking software of the console 122 for accurately displaying on the display screen 124 location and orientation of the needle 166. For example, if geometric and magnetic aspects of the needle 166 do not match up but are known form the needle characteristics, the needle-tracking software is configured to compensate with offsets for the location and orientation of the needle 166.

The single-patient equipment 110 further includes a magnetizer tray 170 configured to magnetize at least the distal-end portion of the needle 166 so as to enable the needle 166 to be tracked with the console 122 and the ultrasound probe 148 of the needle-guidance system 100 during a percutaneous procedure. An exemplary magnetizer tray is disclosed in U.S. Patent Publication No. US 2018/0310955, which is incorporated by reference in its entirety into this application. The magnetizer tray 170 (e.g., a bottom tray of the magnetizer tray 170) can include an RFID reader or RFID reader-writer 172 and an RFID-reader port configured to be connected to the RFID-reader port of the console 122 by a cable. The RFID reader or RFID reader-writer 172 is configured to read the RFID tag for the VAD 164, which enables the console 122 to customize its operation in accordance with the needle characteristics of the needle 166. In addition, the RFID reader-writer 172 is configured to write additional RFID-tag data to the RFID tag. The additional RFID-tag data can include a timestamp for each date and time the RFID-tag data is read from the RFID tag including a starting timestamp and a stopping timestamp. Reading the RFID-tag data from the RFID tag or writing the additional RFID-tag data to the RFID tag can be done while the magnetizer tray 170 magnetizes the needle 166 of the VAD 164 for magnetically tracking the needle 166 with the console 122 and the ultrasound probe 148 of the needle-guidance system 100.

During operation of the needle-guidance system 100, the head of the ultrasound probe 148 is placed against skin of a patient by a clinician, the piezoelectric array 160 emits ultrasonic pulses, and the piezoelectric array 160 receives echoes of the ultrasonic pulses reflected off internal anatomy of the patient proximate a prospective insertion site, thereby producing ultrasonic imagery of the internal anatomy of the patient such as a portion of a vessel beneath the skin of the patient. Such ultrasonic imagery can be depicted on the display screen 124 of the console 122. Further during operation of the needle-guidance system 100, the sensor array 162 of the ultrasound probe 148 detects the magnetic field of the magnet or magnetized region of the needle 166 of the VAD 164. Magnetic field-strength data of the magnetic field of the needle 166 sensed by the magnetic sensors of the sensor array 162 is forwarded to the processor 228 of the console 122, which computes in real time the location and orientation of the needle 166. The location and orientation of the needle 166 of the VAD 164 is accurately determined by the needle-guidance system 100 in accordance with the needle characteristics from the RFID tag, which, in turn, enables the console 122 to superimpose an image of the needle 166 over the ultrasonic imagery on the display screen 124. For example, the ultrasound imagery on the display screen 124 can include a depiction of a skin surface of a patient and a vessel under the skin surface to be accessed by the needle 166 of the VAD 164, as well as a depiction of the needle 166 as detected by the console 122 and the ultrasound probe 148 of the needle-guidance system 100 in accordance with its real time location and orientation with respect to the vessel.

When a needle is not of the VAD 164 or a different VAD not including a catheter, the console 122 can include a catheter-determination algorithm of the algorithms 232 configured to select from look-up tables of the console 122 or the like a catheter of an appropriate gauge for use with the needle in accordance with the needle characteristics. In addition, the console 122 can be configured to display a catheter-gauge icon on the display screen 124 corresponding to an appropriate gauge of catheter. For example, if the clinician navigates to a measurement-tool screen on the display screen 124, the console 122 is configured to pre-select a catheter-gauge icon on the display screen 124 for the appropriate gauge of catheter.

Methods

A method of the needle-guidance system 100 includes a step of obtaining a VAD such as the VAD 164 for use with a patient. The needle 166 of the VAD 164 includes a magnet or a magnetizable region about the distal-end portion of the needle 166. The VAD 164 also has the RFID tag incorporated into the VAD 164 or the packaging for the VAD 164. The method also includes a step of accessing by a clinician the console 122 having the number of ports 226 including the RFID-reader port. The method also includes a step of processing with the processor 238 of the console 122 the instructions of the needle-tracking software provided by the memory 230 of the console 122 for the needle tracking. The method also includes a step of reading the RFID-tag data (e.g., encrypted RFID-tag data, needle characteristics of the needle 166, etc.) from the RFID tag with the RFID reader or RFID reader-writer and, optionally, a step of writing to the RFID tag additional RFID-tag data (e.g., a timestamp for each date and time the RFID-tag data is read from the RFID tag including a starting timestamp and a stopping timestamp) with the RFID reader-writer. The method also includes a step of validating the VAD 164 by way of the RFID-tag data such as by checking the look-up tables or the online database if compatible. The method also includes a step of needle tracking on the display screen 124 of the console 122 after receiving the RFID-tag data from the RFID tag, all of which makes a percutaneous procedure more efficient with the needle-guidance system 100.

The method further includes a step of correctly identifying with the console 122 the needle 166 from the needle characteristics. The method also includes a step of accurately guiding insertion of the needle 166 into the patient on the display screen 124. The method also includes a step of displaying for the clinician on the display screen 124 a location of the needle 166 in the patient.

The method further includes a step of selecting with the catheter-determination algorithm from the look-up tables of the console 122 a catheter of an appropriate gauge for use with a VAD in accordance with the needle characteristics of the VAD if not the VAD 164 having the catheter as set for above.

The method further includes a step of enforcing with the use-enforcement algorithm of the console 122 a predefined maximum number of uses of the VAD 164. The step of enforcing the predefined maximum number of uses of the VAD 164 includes enforcing a single use of the VAD 164.

The method further includes a step of automatically stopping the needle tracking with the console 122 upon exceeding the predefined number of uses of the VAD 164.

The method further includes a step of associating the VAD 164 with an active patient profile for the patient in the patient database of the console 122 by way of the RFID-tag data.

The method further includes a step of simultaneously storing in the device database of the console 122 identifying information for the VAD 164 from the RFID-tag data including any starting and stopping timestamps. The method also includes a step of calculating dwell time for the needle 166 of the VAD 164 in accordance with any of the starting and stopping timestamps.

The method further includes a step of reporting on the display screen 124 a rate of unique VADs from the device database used with the console 122 over one or more periods of time.

The method further includes a step of connecting an RFID-reader port of the RFID reader or RFID reader-writer to the RFID-reader port of the console 122 by a cable. The step of obtaining the VAD 164 includes obtaining the RFID reader or RFID reader-writer as part of the magnetizer tray 170 of the packaging for the VAD 164.

The method further includes a step of magnetizing the magnetizable region of the needle 166 with the magnetizer tray 170 during the step of reading the RFID-tag data from the RFID tag.

The method further includes a step of connecting an RFID-reader port of a handheld RFID reader or RFID reader-writer to the RFID-reader port of the console 122 by a cable. The method also includes a step of reading the RFID-tag data from the RFID tag with the handheld RFID reader or RFID reader-writer each time a procedural event of a number of procedural events is performed. Each procedural event is selected from inserting the needle 166 of the VAD 164 into the patient, drawing blood from the patient, selecting a medication for infusion, infusing the medication into the patient, observing morbidity (e.g., phlebitis, infection), pulling the VAD 164 from the patient, and exchanging the VAD 164. Other procedural events can include cleaning a hub of the VAD 164, capping the hub of the VAD 164, etc. The method also includes a step of logging by the console 122 the procedural events in a procedural event database, which can be used to generate reports for improvements in various procedures.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A needle-guidance system, comprising:
single-patient equipment including a vascular access device ("VAD") having: a needle including a magnet or a magnetizable region about a distal-end portion of the needle configured for magnetically tracking the needle near or in a patient; and
a radiofrequency identification ("RFID") tag incorporated into the VAD or a packaging for the VAD;
multi-patient equipment including a console optionally having a number of ports including an RFID-reader port, wherein the console;
   is configured to automatically start needle tracking for a clinician on an integrated display screen of the console after receiving RFID-tag data from the RFID tag, validating compatibility of the VAD with one or more additional medical devices or a particular percutaneous procedure, and processing with a processor of the console instructions of needle-tracking software provided by memory of the console for the needle tracking;
   is configured to simultaneously store in a device database of the console, identifying information for the VAD from the RFID-tag data as well as starting and stopping timestamps for calculating dwell time for the needle of the VAD; and
   includes a reporting algorithm configured to report on the integrated display screen a rate of unique VADs used with the console over one or more periods of time from the device database; and
an RFID reader-writer configured to read the RFID-tag data from the RFID tag and write additional RFID-tag data to the RFID tag, the RFID reader-writer provided with the packaging for the VAD or the multi-patient equipment, wherein:
   the RFID-tag data includes needle characteristics of the needle, the needle characteristics selected from magnetic strength of the magnet, geometric length of the magnet, magnetic length of the magnet, and magnetic-alignment parameters of magnetic relating offsets of a magnetic-field axis to a physical axis; and
   the additional RFID-tag data includes a timestamp for each date and time the RFID-tag data is read from the RFID tag including a starting timestamp and a stopping timestamp.

2. The needle-guidance system of claim 1, wherein the RFID-tag data is encrypted.

3. The needle-guidance system of claim 1, wherein the needle characteristics are further selected from needle length, needle gauge, and needle bevel.

4. The needle-guidance system of claim 3, the console is configured to correctly identify the needle from the needle characteristics, accurately guide insertion of the needle into the patient, and display for the clinician a location of the needle in the patient on the integrated display screen.

5. The needle-guidance system of claim 3, wherein the console includes a catheter-determination algorithm configured to select a catheter of an appropriate gauge for use with the VAD in accordance with the needle characteristics.

6. The needle-guidance system of claim 1, wherein the console includes a use-enforcement algorithm configured to enforce a predefined maximum number of uses of the VAD.

7. The needle-guidance system of claim 6, wherein the predefined maximum number of uses of the VAD is a single use of the VAD.

8. The needle-guidance system of claim 6, wherein the console is configured to automatically stop the needle tracking upon exceeding the predefined maximum number of uses of the VAD.

9. The needle-guidance system of claim 1, wherein the console includes a patient database configured for associating the VAD with an active patient profile for the patient by way of the RFID-tag data.

10. The needle-guidance system of claim 1, wherein the RFID reader-writer is provided in a magnetizer tray of the packaging for the VAD, the magnetizer tray including an RFID-reader port configured to be connected to the RFID-reader port of the console by a cable.

11. The needle-guidance system of claim 10, wherein the magnetizer tray is configured to magnetize the magnetizable region of the needle while reading the RFID-tag data from the RFID tag.

12. The needle-guidance system of claim 1, wherein the RFID reader-writer is a handheld RFID reader-writer provided with the multi-patient equipment, the handheld RFID reader-writer including an RFID-reader port configured to be connected to the RFID-reader port of the console by a cable.

13. The needle-guidance system of claim 1, wherein the RFID reader-writer is an internal RFID reader-writer of the console provided with the multi-patient equipment.

* * * * *